US007107987B2

(12) United States Patent
Sundaram et al.

(10) Patent No.: US 7,107,987 B2
(45) Date of Patent: Sep. 19, 2006

(54) SPACER FOR DELIVERY OF MEDICATIONS FROM AN INHALER TO CHILDREN AND BREATHING IMPAIRED PATIENTS

(75) Inventors: Shivshankar Sundaram, Madison, AL (US); Balabhaskar Prabhakarpandian, Madison, AL (US); Vinod Makhijani, Guilford, CT (US); Andrzej Przekwas, Huntsville, AL (US)

(73) Assignee: CFD Research Corporation, Huntsville, AL (US)

( * ) Notice: Subject to any disclaimer, the term of this patent is extended or adjusted under 35 U.S.C. 154(b) by 0 days.

(21) Appl. No.: 10/775,465

(22) Filed: Feb. 10, 2004

(65) Prior Publication Data

US 2005/0172955 A1 Aug. 11, 2005

(51) Int. Cl.
*A61M 11/00* (2006.01)
*A61M 15/00* (2006.01)

(52) U.S. Cl. .......................... 128/200.23; 128/200.22; 128/203.15

(58) Field of Classification Search ........... 128/200.23, 128/200.22, 200.18, 200.14, 203.15, 203.18, 128/203.19
See application file for complete search history.

(56) References Cited

U.S. PATENT DOCUMENTS

| | | | | | |
|---|---|---|---|---|---|
| D34,779 | S | | 7/1901 | McPherson | |
| 4,174,712 | A | | 11/1979 | Moren et al. | 128/173 |
| 4,222,126 | A | | 9/1980 | Boretos et al. | 3/1.5 |
| 4,470,412 | A | | 9/1984 | Nowacki et al. | 128/200.2 |
| 4,484,577 | A | | 11/1984 | Sackner et al. | 128/203.3 |
| 4,706,663 | A | | 11/1987 | Makiej | 128/200.2 |
| 4,790,305 | A | | 12/1988 | Zoltan et al. | 128/200.2 |
| 5,007,419 | A | | 4/1991 | Weinstein et al. | 128/200.2 |
| 5,012,803 | A | | 5/1991 | Foley et al. | 128/200.2 |
| 5,042,467 | A | * | 8/1991 | Foley | 128/200.23 |
| 5,178,138 | A | * | 1/1993 | Walstrom et al. | 128/200.23 |
| 5,203,323 | A | | 4/1993 | Tritle | 128/200.2 |
| 5,297,543 | A | | 3/1994 | Larson et al. | 128/200.2 |
| 5,385,140 | A | | 1/1995 | Smith | 128/200.2 |
| 5,427,089 | A | | 6/1995 | Kraemer | 128/200.2 |
| D362,500 | S | | 9/1995 | Cook et al. | 24/110 |
| 5,477,849 | A | | 12/1995 | Fry | 128/200.2 |
| D373,630 | S | | 9/1996 | Berg et al. | 24/110 |
| D380,663 | S | | 7/1997 | Nakamura | 8/354 |
| 5,645,049 | A | | 7/1997 | Foley et al. | 128/203.3 |
| 5,699,789 | A | | 12/1997 | Hendricks | 128/203.2 |
| 5,724,962 | A | | 3/1998 | Vidgren et al. | 128/205.2 |
| D394,313 | S | | 5/1998 | O'Brien | 24/110 |
| 5,775,320 | A | | 7/1998 | Patton et al. | 128/200.1 |
| 5,809,996 | A | * | 9/1998 | Alldredge | 128/200.23 |
| 5,816,240 | A | | 10/1998 | Komesaroff | 128/200.2 |
| 5,839,430 | A | | 11/1998 | Cama | 128/200.1 |

(Continued)

*Primary Examiner*—Henry Bennett
*Assistant Examiner*—Amadeus Lopez
(74) *Attorney, Agent, or Firm*—Tomas Friend

(57) ABSTRACT

A spacer for delivering a medication spray from an inhaler includes a first conical body joined to a second conical body, forming a continuous spray conduit through first and second internal chambers of the respective first and second conical bodies. A mouthpiece is formed in the proximal end of the first conical body. A spray inlet for attachment to the inhaler is formed at the distal end of the second conical body. A plurality of air inlets are placed downstream of the medication inlet proximate to, or in, the large diameter distal end surface of the first conical body. Recirculation zones are created in the first and second chambers, to force the medication spray into a central airflow path through the spray conduit, minimizing particle deposition by contract with the walls of the spacer.

15 Claims, 13 Drawing Sheets

U.S. PATENT DOCUMENTS

| | | | |
|---|---|---|---|
| 5,848,588 A | 12/1998 | Foley et al. | 128/200.2 |
| 5,875,776 A | 3/1999 | Vaghefi | 128/203.2 |
| 5,899,201 A * | 5/1999 | Schultz et al. | 128/200.23 |
| D412,979 S | 8/1999 | Weinstein et al. | 24/110 |
| 5,938,118 A | 8/1999 | Cooper | 239/102.2 |
| D416,621 S | 11/1999 | Forssell et al. | 24/110 |
| 5,983,893 A | 11/1999 | Wetterlin | 128/203.2 |
| 5,988,160 A | 11/1999 | Foley et al. | 128/200.2 |
| D420,736 S | 2/2000 | Moulin | 24/110 |
| 6,026,807 A * | 2/2000 | Puderbaugh et al. | 128/200.23 |
| 6,039,042 A | 3/2000 | Sladek | 128/200.2 |
| D422,884 S | 4/2000 | Lafond | 8/354 |
| D428,486 S | 7/2000 | Schuckmann | 24/110 |
| D435,212 S | 12/2000 | Philippe | 8/354 |
| 6,202,643 B1 | 3/2001 | Sladek | 128/200.2 |
| D442,685 S | 5/2001 | Sladak | 24/110 |
| 6,234,169 B1 | 5/2001 | Bulbrook et al. | 128/203.2 |
| 6,293,279 B1 | 9/2001 | Schmidt et al. | 128/200.2 |
| D450,117 S | 11/2001 | Braithwaite et al. | 24/110 |
| D452,910 S | 1/2002 | Braithwaite et al. | 24/110 |
| 6,336,455 B1 | 1/2002 | Howlett | 128/203.2 |
| 6,347,629 B1 * | 2/2002 | Braithwaite | 128/200.15 |
| 6,363,932 B1 | 4/2002 | Forchione et al. | 128/203.1 |
| 6,367,471 B1 | 4/2002 | Genosar et al. | 128/200.2 |
| 6,435,176 B1 * | 8/2002 | Berg et al. | 128/200.23 |
| 6,595,206 B1 * | 7/2003 | Vito | 128/200.23 |
| 6,615,826 B1 * | 9/2003 | Gabrio et al. | 128/200.23 |
| 2002/0121275 A1 | 9/2002 | Johnson et al. | 128/200.2 |
| 2003/0029447 A1 | 2/2003 | Vito | 128/200.2 |
| 2004/0094148 A1* | 5/2004 | Lulla et al. | 128/200.23 |

* cited by examiner (a)

(b)

(a)            (b)

SPACER FOR DELIVERY OF MEDICATIONS FROM AN INHALER TO CHILDREN AND BREATHING IMPAIRED PATIENTS

STATEMENT REGARDING FEDERALLY SPONSORED RESEARCH OR DEVELOPMENT

Work on this invention was performed under NIH Grant R44HL64500-03 titled "Development of an Improved Pediatric Spacer for Inhalers" during the period May 2000 through November 2000 and from October 2002 through the date of filing. Accordingly, the U.S. Government may have rights in the invention.

CROSS-REFERENCES TO RELATED APPLICATIONS

Not Applicable

REFERENCE TO SEQUENCE LISTING OR COMPUTER PROGRAM LISTING APPENDIX

Not Applicable

BACKGROUND OF THE INVENTION

The present invention relates generally to devices for use in orally dispensing medication using an inhaler. More specifically, the present invention relates to spacers used for facilitating the delivery to pediatric and breathing impaired patients of medication dispensed from an inhaler.

Medications are commonly dispensed from pressurized metered dose inhalers (MDI) to deliver the medication directly to the lungs of a patient. Spacers are used for transporting the medication from the spray outlet of the MDI to the patient's mouth. The spacer is intended to increase the effectiveness of drug delivery to the deep lung regions of the patient primarily by decelerating the drug spray before the spray enters the patient's mouth. The spacer will also reduce the size of spray droplets (by evaporation) and trap larger particles in the spacer. This will reduce the need for hand-breath coordination and allow for multiple breath inhalation therapy, thereby improving the overall delivery of the medication dose to the lung. These factors are particularly important when trying to effectively provide inhalation therapy to children and to patients with breathing impairments.

The quantity, size, and velocity of the drug particles that exit an inhalation spacer are affected by dynamic interactions between the spacer, spray properties, and airflow. Unfortunately, in conventional spacers, as much as 50% of the medication is lost before delivery to the patient because of inefficient design of the spacer itself. For example, high-pressure, recirculation zones are created near sharp corners in the spacer. These recirculation zones trap spray particles and provide increased time for particle deposition on the spacer walls such that they are not delivered to the patient. Also, while it is known that medication particles having a diameter in the range of 3–5 microns are desirable for delivery to deep lung tissue, conventional spacers do a poor job of consistently delivering particles of this size. This is because existing spacer designs do not effectively control the heat exchange rate and the length of time that the medication particles remain inside the spacer, factors which directly affect particle size. Finally, prior art spacers typically include air inlets at the upstream (spray discharge) end near the mouthpiece but they cannot maintain consistent flow energy. All of these factors will cause undesirable deposition of the medication droplets in the oro-pharyngeal region of the patient. The inefficient delivery of medication to the deep lung results in either under-medication of the patient or the waste of expensive medications.

U.S. Pat. No. 6,367,471 discloses an internal vortex mechanism for an inhaler device. More specifically, vortex generators positioned within the wall of the conduit and in fluid communication with air inlets for receiving ambient outside air, provide the inner wall of the conduit with a circumferential-swirling turbulent boundary layer flow to minimize impaction of the medication on the inner surfaces of the conduit. The inhaler device shown in FIG. 1 of the patent contains only one chamber. The apparatus also includes a medication dispenser supported in the housing and adapted to dispense a dose of aerosolized medication into the conduit, a plurality of air inlets positioned on the outer surface of the conduit and a plurality of vortex generators positioned within the wall of the conduit downstream of the medication dispenser. Each vortex generator includes a first generally pyramid-like portion having an apex and an open base forming an outlet located on the inner surface of a second generally pyramid-like portion having an apex and an open base in fluid communication with a corresponding air inlet.

U.S. Patent Application Publication 2002/0121275 discloses an aerosol enhancement device. More specifically, the aerosol enhancement device displayed in FIGS. 1–6 provides a single chamber. The air inlet port is positioned centrally with respect to the spacer.

U.S. Pat. No. 6,234,169 discloses an inhaler. The inhaler provides a conduit defining an air flow path extending between the first end and the second end and an orifice in the chamber between the first end and the second end, the orifice utilizing the Coanda Effect when the reservoir is in air flow communication with the chamber and upon inhalation by the individual to draw medication from the reservoir. As seen in FIGS. 1–6, the inhaler has only a single chamber with the positions of air inlet shown in the Figures.

What is needed, then, is a spacer and method of use thereof for the efficient delivery of medication from a metered dose inhaler, through the spacer, and into the patient. Such a spacer would be easy to use and substantially improve the delivery of medication to the patient's lungs.

BRIEF SUMMARY OF THE INVENTION

The design of the spacer of the present invention effectively channels the spray down the centerline of the spacer and limits contact between medication particles and the walls of the spacer (deposition). Further, the spacer of this invention minimizes the formation of any adverse recirculation zones that trap medication particles within the spacer. Rather, by a careful and novel design, the present invention creates and takes advantage of high-pressure recirculation zones that tend to force the medication spray away from the walls of the spacer and into a preferred, central spray pattern. Consequently, the spacer of the present invention delivers a higher percentage of the medication to the deep lung regions of the patient.

To accomplish this, one embodiment of the spacer of the present invention includes a first conical body joined to a second conical body, forming a continuous spray conduit through first and second internal chambers of the respective first and second conical bodies. A mouthpiece is formed in the small diameter (proximal, downstream) end of the first conical body. A spray inlet for attachment to an MDI or similar device is formed at the large diameter (distal, upstream) end of the second conical body. A plurality of air inlets are placed downstream of the medication inlet proximate to, or in, the large diameter distal end surface of the first conical body. During use, high-pressure air recirculation zones are created in the first and second chambers, near the spray inlet and the air inlets, and an air jacket is created along the inner surface of the wall of the first conical body. This forces the medication spray through the spacer into a defined airflow path through the spray conduit, minimizing particle entrapment and contact with the walls of the spacer.

In one embodiment of the spacer a unidirectional valve is provided proximate the mouthpiece. In another embodiment, the spacer is provided with at least one conical body that is collapsible, so that the spacer will occupy less storage space when not in use.

BRIEF DESCRIPTION OF THE SEVERAL VIEWS OF THE DRAWINGS

FIGS. 14(a), (b) and (c) are rear views showing different geometries of the alternate embodiment adapter of FIG. 13.

FIG. 15 graphically shows the distribution of medication particle sizes delivered by the spacer of the present invention as compared to conventional spacers.

FIG. 16 graphically shows experimental performance data comparing the spacer of the present invention to conventional spacers, using an Andersen cascade impactor and conventional testing protocols.

FIG. 17 is a side view of showing the dimensions of the embodiment of the spacer used in obtaining the performance results shown in FIG. 16.

DETAILED DESCRIPTION OF THE INVENTION

Figure 1:
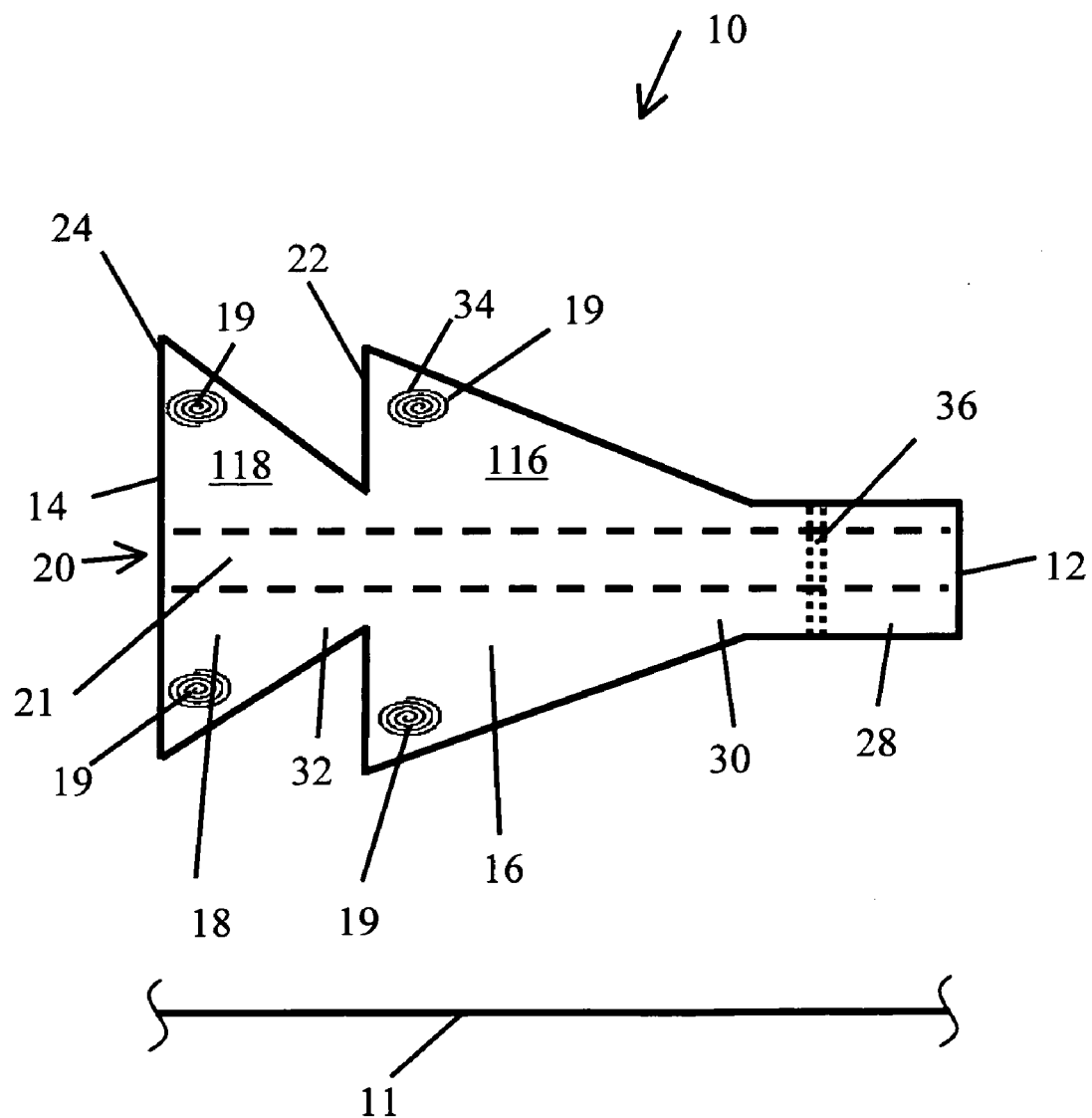
FIG. 1 is a cross sectional side view of one embodiment of the spacer, further schematically illustrating flow of medication and the location of recirculation zones located within the chambers of the spacer.
Figure 2:
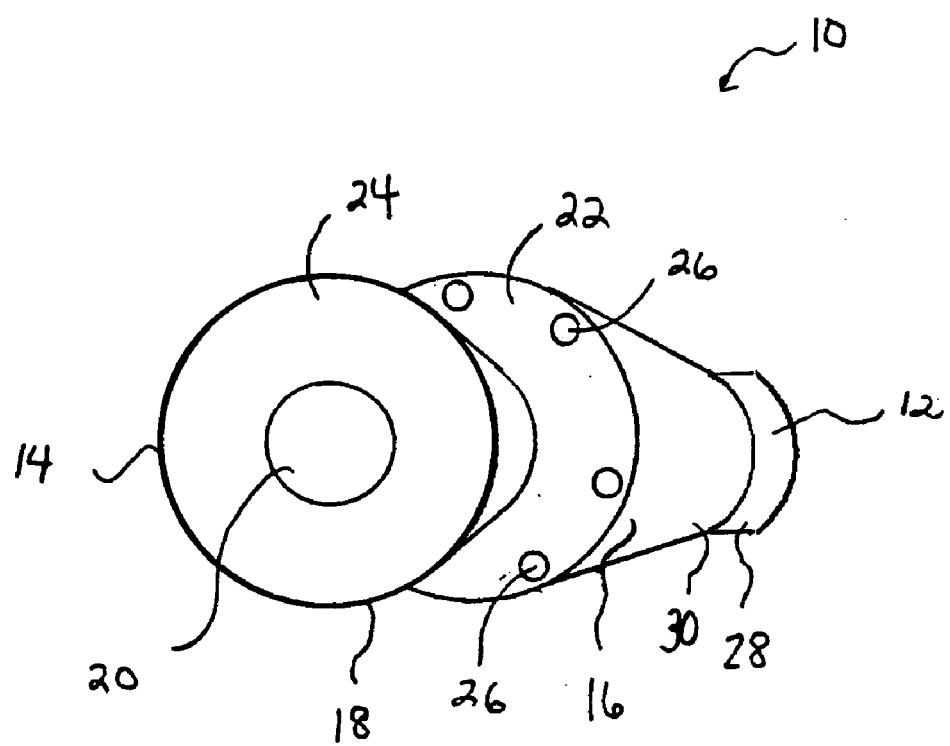
FIG. 2 is a perspective view of the spacer of FIG. 1, looking from the spray inlet at the distal end of the spacer.

Referring to FIGS. 1 and 2, the spacer of the present invention 10 includes spacer walls defining a first conical body 16 having a small diameter proximal end 30, a large diameter distal end 34, and a distal end surface 22. The central portion of the distal end surface 22 of the first conical body is joined to, and in fluid communication with, a small diameter proximal end 32 of a second conical body 18. The first and second conical bodies 16, 18 have respective first and second internal chambers 116, 118 that generally define a continuous spray conduit 11 through the spacer 10 from the distal end 14 of the second conical body 18 to the proximal end 30 of the first conical body 16. Preferably, a mouthpiece 28 will be formed in (or attached to) the proximal end 30 of the first conical body 16 such that the spray conduit 11 extends to the proximal end 12 of the spacer 10. A spray inlet 20 (FIG. 2) for attachment of an MDI or other medication dispensing inhaler is centrally provided in the distal end surface 24 at the distal end 14 of the second conical body 18.

Looking more particularly at FIG. 2, a plurality of circumferential air inlets 26 are provided within the distal end surface 22 of the first conical body 16, to allow external air to pass into the first chamber 116. This external air supply is known to be needed to make-up (in addition to the small drug volume) the required inhalational air volume, and thereby prevent vacuum formation. However, as will be explained in more detail below, in the present invention the air inlets 26 are strategically placed in a location downstream from the spray inlet 24. Here the momentum of the air stream (velocities ~5 m/s) is comparable to that of the medicinal spray, unlike at the discharge end where the spay velocities are in excess of 50 m/s. This external, circumferential airflow provides a jacket, which minimizes spray contact with the walls of the first chamber 116. It also contributes to the creation of recirculation zones 19 in the first chamber 116, and recirculation zone 19 in the now closed (unlike other spacers) second chamber 118, which also serve to constrain the movement of the medication spray to a general spray path 21 through the spacer 10. All of these features decrease the amount of drug deposited in the spacer and increase drug delivery to the patient.

Briefly, the method of providing an inhaled medication to the deep lung of a pediatric or breathing impaired patient includes dispensing a medication spray into the spray inlet 14 of a spacer 10, controlling the spray path 21 in the spacer 10 at least in part by creating recirculation zones 19 downstream of the spray inlet 14 so that only a minimal amount of the medication contacts the interior surfaces of the spacer 10.

Figure 6:
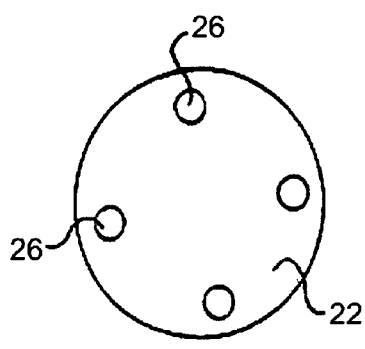
FIG. 6 is a distal end view of the first conical body of the spacer, illustrating the orientation of the downstream air inlets.
Figure 6:
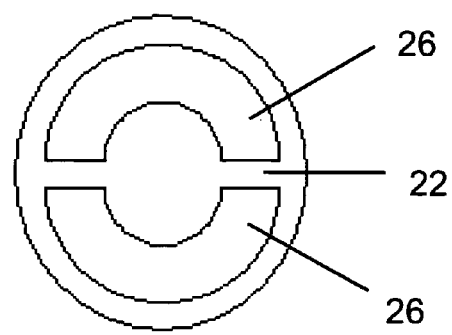

As more particularly shown in FIG. 6, in one embodiment of the spacer 10, the air inlets 26 are formed integral to the large diameter distal end surface 22 of the first conical body 16. In such embodiments, the air inlets 26 assist in limiting drug impaction loss by channeling the spray centrally down the spacer path due to judicious use of the external airflow momentum and generation of recirculation zones 19. The plurality of air inlets 26 may be evenly spaced about the large diameter end surface 22. In another embodiment shown in FIG. 6(b), the air inlet can be a fully circumferential slot with support structures.

Figure 3:
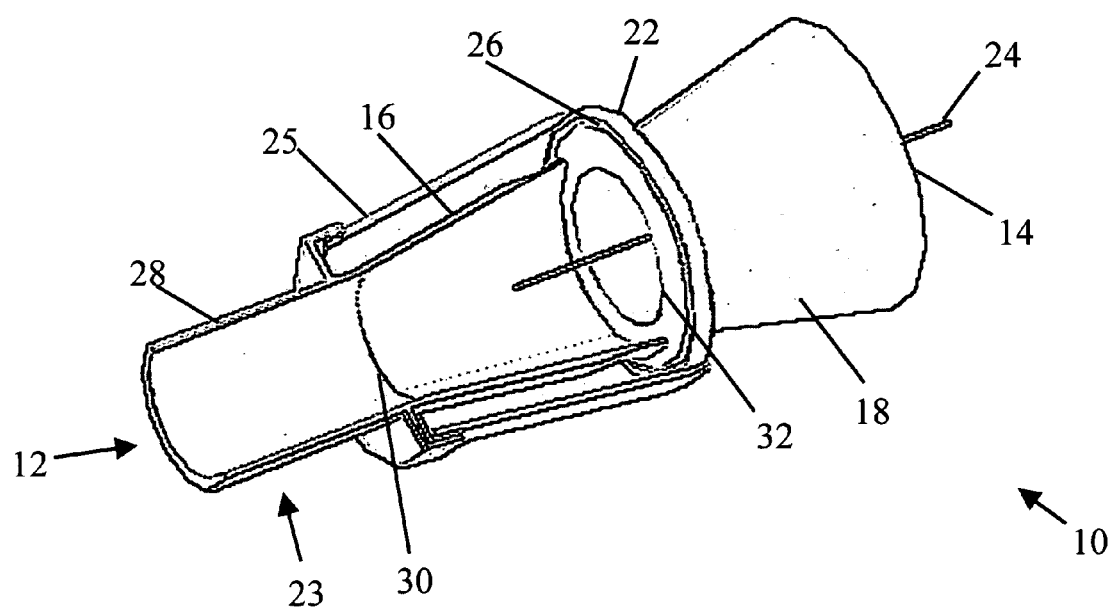
FIG. 3 is a partially cutaway side view of a variation of the spacer of FIGS. 1 and 2, showing a portion of the first conical body collapsed into the first chamber for storage purposes.
Figure 4:
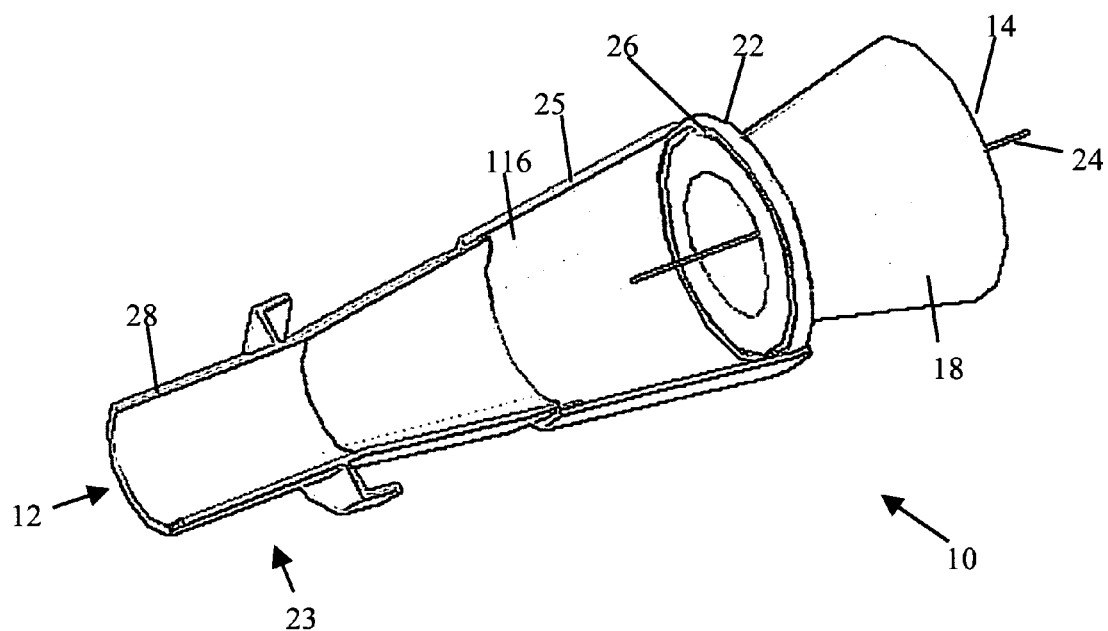
FIG. 4 is a partially cutaway side view of the spacer of FIG. 3, with the first conical body in the extended position for use.

As shown in FIGS. 3 and 4, the spacer 10 may be collapsible. As shown in FIG. 3, a proximal section 23 of the first conical body 16 can retract into a distal section 25 along the outwardly tapered wall when not in use, thereby reducing the overall length of the spacer 10 for ease of storage and portability. As shown in FIG. 4, the proximal section 23 of the first conical body 16 can then be pulled out manually, thereby extending the effective length of the spray conduit 11 (FIG. 1) for use. The sliding motion of the proximal section 23 relative to the distal section 25 results in an air-tight first chamber 116 through which the medication travels. In one embodiment, the two sections provide an air tight seal enabled by a friction fit. A locking ring may be provided so that the two sections are held together in the collapsed state.

The spacer 10 may be constructed of any biologically inert material which is suitable for the intended function. Examples of the types of materials that may be used for the construction of the spacer include plastic, rubber, and light metal Some of the preferred materials are Polypropylene and PMMA (preferably additionally treated with permanent electrostatic discharge protection) and anodized metals (for example, aluminum) for the body. Silicone rubber may be used for the valve and the adapter. The spacer 10 may be manufactured as a single integral piece, or in multiple parts which may then be bonded or removably attached for use.

Figure 8:
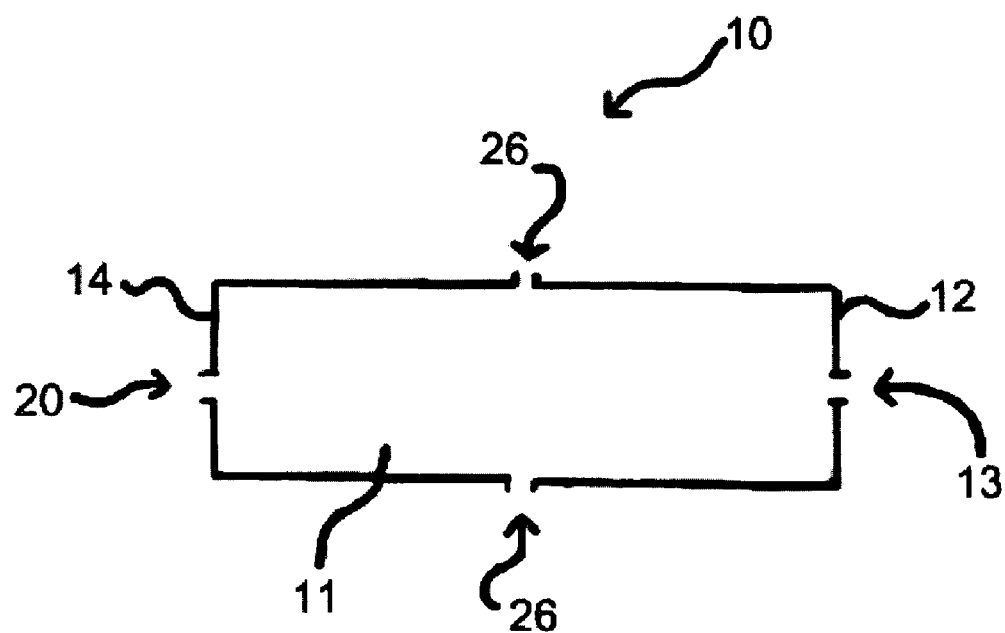
FIG. 8 is a schematic illustration of the continuous spray conduit (21) extending between the proximal (downstream) and upstream (distal) ends of the spacer as well as the downstream air inlets.

As noted above, the geometry of the spacer 10 and the downstream air inlets 26 cooperate to generate one or more recirculation zones 19 inside the chambers 116, 118 when the medication spray enters the spacer 10. The recirculation zones 19 provide two benefits. First, they reduce undesirable contact between the medication particles and the walls of the spacer 10. Second, they tend to constrain the spray to a defined spray path 21 (FIG. 1) through a central portion of the chambers 116, 118. This reduces entrapment of medication particles in the spacer 10, maintains flow energy, and maintains proper particle duration and heat exchange rates within the chambers 116, 118. FIG. 8 schematically shows the arrangement of the air inlets 26 with respect to the upstream (distal) end 14 and a downstream (proximal) end 12. The air inlets 26 may be circular or oblong shape or may be formed as a rectangular slot.

Modifications to the location, size, number, and shape of the air inlets 26 impact the generation and function of the recirculation zones 19. Additionally, the shapes of the first chamber 116 and second chamber 118 are also involved in determining the functionality of the recirculation zones 19. Accordingly, the air inlets 26 and the shapes of the chambers 116, 118 have a critical impact upon the amount of medication which impacts the walls of the spacer 10 and is not available for inhalation by the patient. Although this invention is not bound by mechanism or theory, high pressure recirculation zones are generated by the propulsion of the medication spray into the spacer 10 in combination with the air which enters the spacer 10 through the air inlets 26 and the number and geometry of the chambers of the spacer 10. Computer simulation techniques based on principles of computational fluid dynamics may be used to optimize chamber and air inlet geometries.

For example, certain physical embodiments of the spacer 10 of the present invention can effectively utilize high-pressure recirculation zones an dair inflow energy to increase the efficacy of drug delivery to the deep lung as compared to conventional spacers, while maintaining drug particle sizes in the desired range of 3.0 to 5.0 microns.

Accordingly, in certain embodiments of the spacer 10, the first conical body will have an axial length of approximately 80 mm, a small (proximal end) diameter of approximately 1 mm, and a large (distal end) diameter of approximately 22 mm. The second conical body will have an axial length of approximately 40 mm and the size of the proximal and distal ends are similar to the first conical chamber. In this embodiment, two rectangular (oblong) air inlets 26 having a diameter of approximately 1 mm are evenly distributed about the distal end surface 22 of the first conical body 16.

Figure 5:
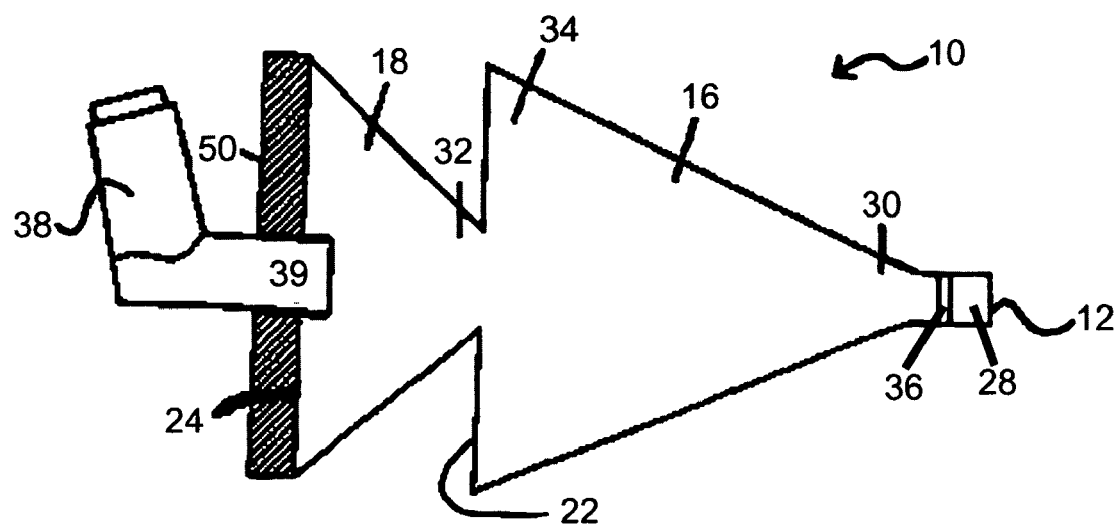
FIG. 5 is a cutaway side view of another embodiment of the spacer showing a unidirectional valve proximate the mouthpiece and further showing the spray outlet of an MDI positioned for ejecting a medication spray into the spray inlet of the spacer.
Figure 7:
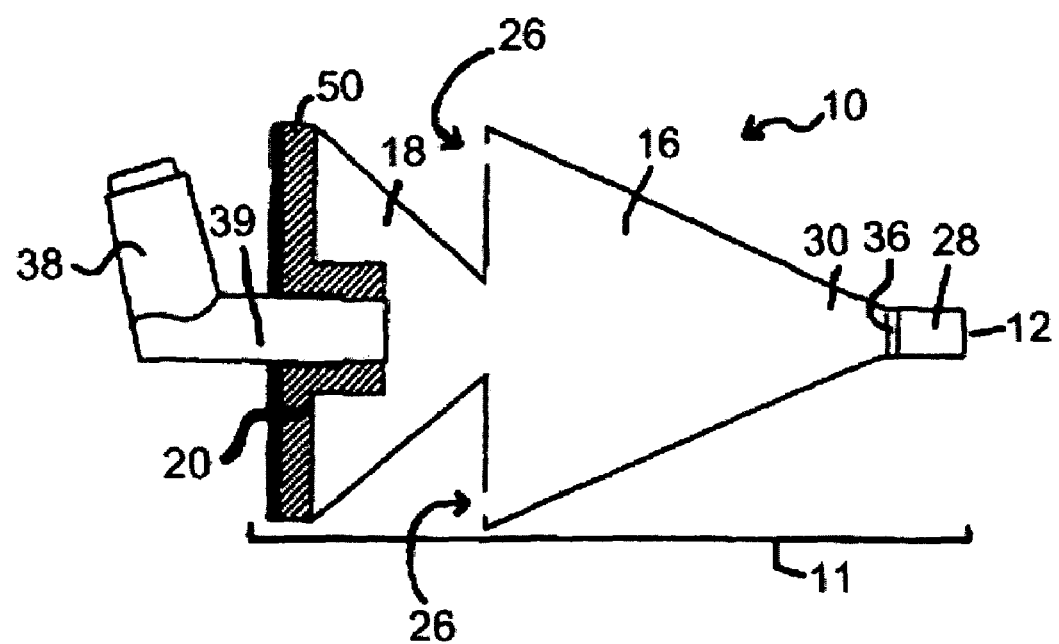
FIG. 7 is a cutaway side view of another embodiment of the spacer, showing the use of an adapter which is used to attach the MDI at the spray inlet of the spacer.
Figure 12:
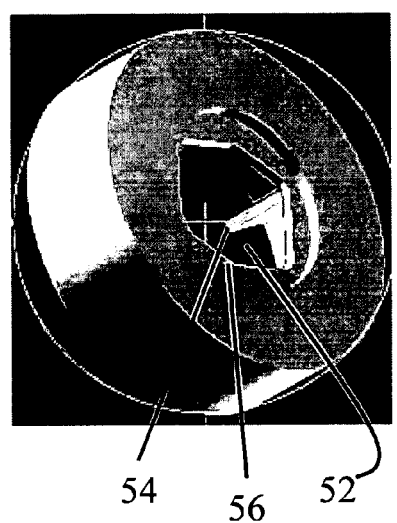
FIG. 12 is a perspective view of the rear (a) and front (b) view of the adapter used in the spacer embodiment of FIG. 7.
Figure 12:
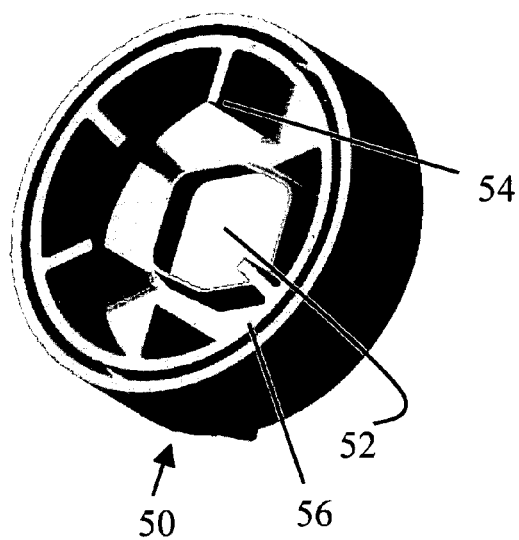
Figure 13:
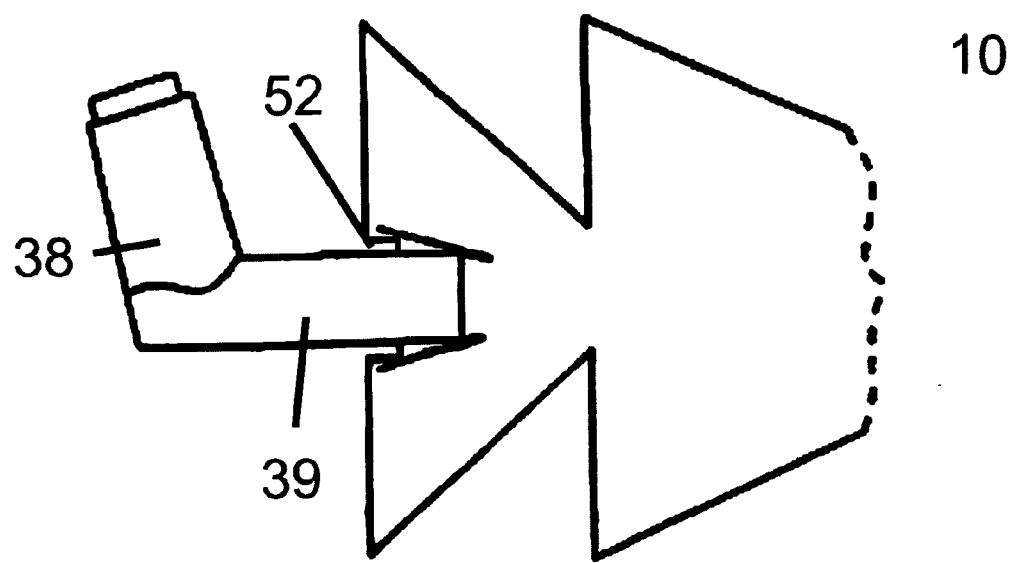
FIG. 13 is a schematic drawing of an alternate embodiment of the adapter used in the spacer of FIG. 7.

Referring now to FIGS. 5, 7 and 12, the spacer 10 of the present invention is shown with an adapter 50 configured to engage a conventional metered does inhaler 38 such that the spray outlet 39 of the inhaler 38 is secured and positioned to deliver a medication dose or spray into spray inlet 20. The adapter 50 may be fully integrated with the spacer 10 during the molding procedure, such that the adapter 50 is made of the same material as the spacer 10. In alternate embodiments, the adapter 50 may be a removable piece which is attached to the spacer 10. The adapter 50 has a flexible opening 52, as shown in FIG. 12. Materials which may be used for constructing the adapter 50 include rubber, soft plastics, or metals such as aluminum, which are well known to those in the art. Spokes 54 are arranged around the adapter opening 52 to maintain correct alignment of the spray outlet 39 with the spray inlet 20. As shown in FIG. 13, the adapter opening 52 can taper inwardly to prevent over-penetration of the spray outlet 39. As shown in FIG. 12, an O-ring 56 may be used to further promote proper alignment and inhibit over-penetration.

FIGS. 14(a)–(c) illustrate different embodiments of the opening 52 of the adapter 50. The opening 52 may be octagonal (c), circular (b), or oblong (a). The opening 52 forms an air-tight seal between the adapter 50 and the medication dispenser 38.

As shown in FIGS. 1–7, a unidirectional valve 36 may be provided at the proximal end 30 of the first conical body 16. Certain patients, such as the elderly and the young, frequently do not inhale at the proper time to maximize oral intake of medication into the deep lung. Accordingly, in addition to the spacer 10 assisting with the deposit of medication within the deep lungs of the patient, a unidirectional, or one-way, valve is useful to allow the patient to inhale the medication while preventing the patient from exhaling and expelling the medication from the spacer 10.

Figure 9:
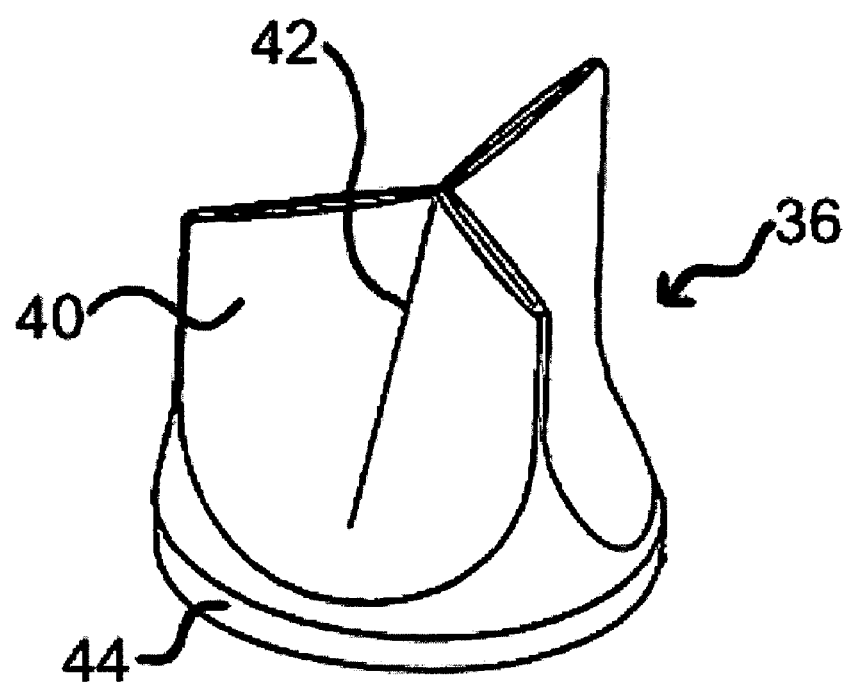
FIG. 9 is a perspective view of one embodiment of a unidirectional valve which may be used within the spacer of the present invention.
Figure 10:
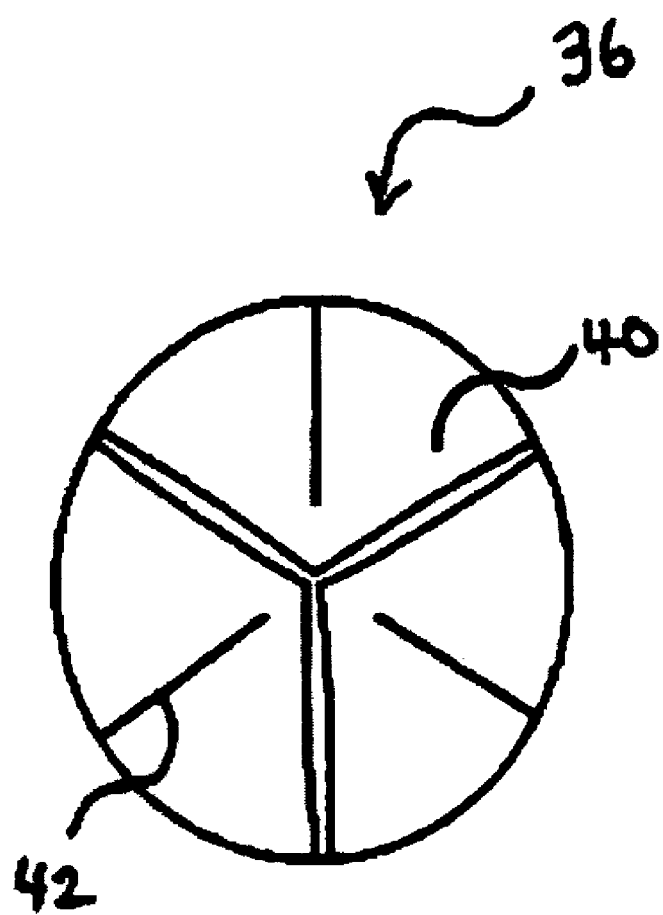
FIG. 10 is a top view of the unidirectional valve of FIG. 9.
Figure 11:
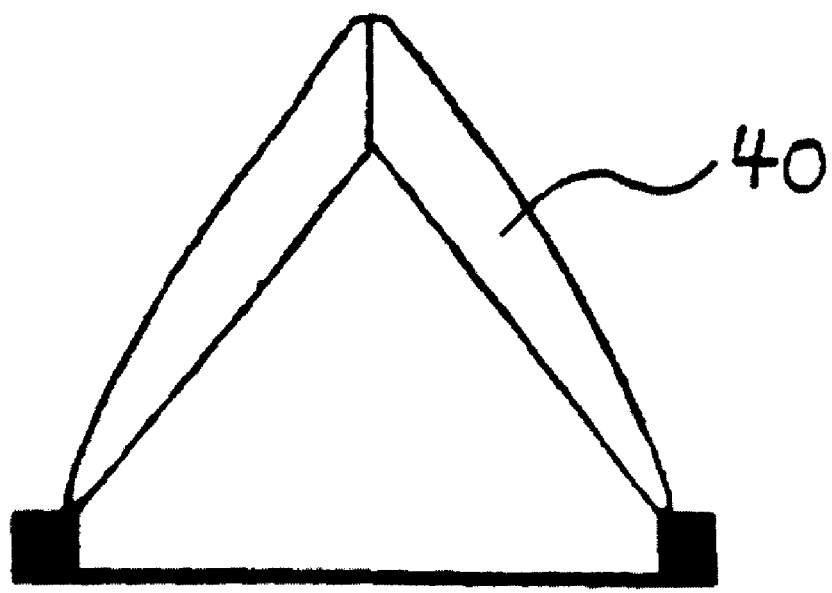
FIG. 11 is a cross sectional side view of the unidirectional valve of FIGS. 9 and 10.

The one-way valve 36 may be a tri-leaflet valve as shown in FIGS. 9–11. Other one-way valves known in the art, such as bi-membrane or single membrane valves, may be also be used. In one embodiment, the tri-leaflet valve is fabricated in a single piece. In an alternate embodiment, three one-piece membranes 40 are supported by spokes 42, as shown in FIG. 10. The valve membrane(s) and supporting spokes 42, if present can rest on an O-ring 44. Each of the membranes 40 is constructed of a thick material at the position most distal from the O-ring 44 and with thinner material more proximate to the O-ring 44, as shown in FIG. 11. The thickness of the material will help maintain a strong seal between the membranes 40 and prevent the membranes 40 from opening in reverse. In an alternate simpler configuration, the valve is held in place between the spacer first chamber 116 and the mouthpiece 28 by a friction fit. The unidirectional valve 36 provides the advantage of allowing an increased air flow for a given suction, or inhalation pressure. The unidirectional valve 36 also minimizes backflow when the user or patient exhales. The unidirectional valve 36 also minimizes the amount of medication which is deposited on the valve surface.

As shown by performance testing, the spacer 10 of the present invention provides improved results with regard to the delivery of medication as compared to other commercially available spacers. As shown in FIG. 15, the spacer 10 of the present invention (labeled "CFDRC") delivers a higher percentage of drug particles with sizes in the preferred range of 3–5 microns. Also, the present invention delivered a greater fraction of drug to the patient, as shown in FIG. 16. The dimensions of the spacer used to achieve the results shown in FIGS. 15 and 16 are shown in FIG. 17.

Although a preferred embodiment of the spacer has been described as having first and second bodies or chambers with a conical geometry, the spacer 10 can also be configured with elliptical bodies or oblong bodies.

Thus, although there have been described particular embodiments of the present invention of a new and useful "Spacer for Delivery of Medications from an Inhaler to Children and Breathing Impaired Patients" it is not intended that such references be construed as limitations upon the scope of this invention except as set forth in the following claims.

What is claimed is:

1. A spacer for delivering a medication spray into the lungs of a patient, the medication spray dispensed by an inhaler into the spacer, the spacer comprising:
   a. a first conical body having a large diameter distal end and a small diameter proximal end;
   b. a second conical body having a large diameter distal end and a small diameter proximal end joined to the distal end of the first conical body;
   c. a mouthpiece positioned at the proximal end of the conical first body;
   d. a spray inlet positioned at the distal end of the second conical body to receive a medication spray dispensed by an inhaler;
   e. the first conical body further comprising a first internal chamber and the second conical body comprising a second internal chamber, the first and second internal chambers forming an unobstructed, linear spray conduit having a continuous spray passage from the spray inlet to the mouthpiece; and
   f. a plurality of air inlets passing through the first body to allow external air to pass into the first body, the air inlets positioned downstream from the spray inlet near the distal end of the first body.

2. The spacer of claim 1, wherein the plurality of air inlets are evenly spaced around the first body.

3. The spacer of claim 1 wherein the first body includes a large diameter distal end surface and wherein the air inlets are positioned in the large diameter distal end surface.

4. The spacer of claim 3 further comprising a one-way valve proximate the mouthpiece, the one-way valve functional to allow the patient to inhale but not exhale through the spray passage in the spacer.

5. The spacer of claim 1 wherein the cross-section each of the first and second conical bodies are elliptical.

6. A spacer for delivering a medication spray ejected by an inhaler external to the spacer to the lungs of a patient through the patient's mouth, the spacer comprising:
   a. a conduit having a proximal end and a distal end;
   b. a spray inlet attached to the distal end of the conduit, the spray inlet adapted for receiving the medication spray from the inhaler;
   c. a mouthpiece attached to the proximal end of the conduit;
   d. the conduit including at least one interior chamber defining an unobstructed, linear spray passage from the spray inlet to the mouthpiece; and
   e. at least one air inlet passing through the wall of the conduit to allow external air to pass into the conduit, the air inlet positioned downstream from the spray inlet.

7. The spacer of claim 6 further comprising a unidirectional valve functionally positioned within the spray passage proximate the mouthpiece.

8. The spacer of claim 7 wherein the unidirectional valve comprises a tri-leaflet valve.

9. The spacer of claim 7, the conduit comprising a first conical section joined end to end with a second conical section.

10. The spacer of claim 9, wherein the first conical section includes a large diameter distal end surface joined to a small diameter proximal end of the second conical section, and wherein the at least one air inlet is positioned in the distal end surface of the first conical section.

11. The spacer of claim 10, further comprising a plurality of air inlets evenly spaced around the distal end surface of the first conical section.

12. A spacer apparatus for transmitting medication to patients after the medication is dispensed by an inhaler external to the inhaler, the spacer comprising:

a mouthpiece;
   a first chamber, the first chamber having a proximal end connected to the mouthpiece;
   a second chamber, the second chamber having a proximal end connected to a distal end of the first chamber;
   a spray inlet connected to a distal end of the second chamber, the spray inlet adapted to receive a medication spray from an inhaler,
   an unobstructed linear internal spray path defined from spray inlet to the mouthpiece, through the first chamber and the second chamber, and
   a plurality of air inlets passing through the apparatus to allow external air into the first chamber.

13. The apparatus of claim 12, wherein the first chamber and the second chamber are converging chambers, wherein a diameter of the proximal ends of each chamber are smaller than a diameter of the distal ends of each chamber.

14. The apparatus of claim 12 wherein the plurality of air inlets have an oblong shape.

15. The apparatus of claim 12 wherein the plurality of air inlets are circular.

* * * * *